(12) United States Patent
Malton et al.

(10) Patent No.: US 6,893,647 B1
(45) Date of Patent: May 17, 2005

(54) COSMETIC COMPOSITIONS

(75) Inventors: Peter James Malton, Egham Surrey (GB); Lynette Anne Makins Holland, Hertfordshire (GB); George Rizzi, Cincinnati, OH (US); Gabor Heltovics, Egham Surrey (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/979,424

(22) PCT Filed: May 5, 2000

(86) PCT No.: PCT/US00/12417

§ 371 (c)(1),
(2), (4) Date: Nov. 6, 2001

(87) PCT Pub. No.: WO00/67720

PCT Pub. Date: Nov. 16, 2000

(51) Int. Cl.$^7$ ............... A61K 6/00; A61L 9/01
(52) U.S. Cl. ............... 424/401; 424/76.1
(58) Field of Search ............... 424/401, 76.1

(56) References Cited

FOREIGN PATENT DOCUMENTS

| | | |
|---|---|---|
| EP | 0 646 602 A | 4/1995 |
| EP | 0 859 047 A | 8/1998 |
| FR | 2 693 728 A | 1/1994 |
| JP | 62/161720 A2 | 7/1987 |
| JP | 63/192706 A2 | 8/1988 |
| JP | 02/117994 A | 5/1990 |
| JP | 50/63126 A2 | 3/1993 |
| JP | 7/241333 A2 | 9/1995 |
| JP | 8/176587 A2 | 7/1996 |
| JP | 10/120541 A2 | 5/1998 |
| JP | 10/263062 A | 10/1998 |
| WO | WO 96/04937 | * 2/1996 |
| WO | WO 96/04937 A | 2/1996 |
| WO | WO 96/04940 A | 2/1996 |
| WO | WO 96/04940 | * 2/1996 |
| WO | WO 98/56341 | * 12/1998 |
| WO | WO 98/56342 A | 12/1998 |
| WO | WO 98/56342 | * 12/1998 |

* cited by examiner

*Primary Examiner*—Shaojia Anna Jiang
(74) *Attorney, Agent, or Firm*—Kenya T. Pierre; Dara M. Kendall; Tara M. Rosnell

(57) ABSTRACT

According to the present invention there is provided fragrance compositions comprising (a) fragrance; and (b) cyclic oligosaccharides having one or more unsubstituted alkyl substituents; wherein the weight ratio of (a) to (b) is at least about 1:1. The compositions of the present invention provide a long-lasting fragrance while at the same time having a 'burst' of fragrance on application.

11 Claims, No Drawings

COSMETIC COMPOSITIONS

FIELD OF THE INVENTION

The present invention relates to cosmetic compositions and in particular to long-lasting fragrance compositions.

BACKGROUND TO THE INVENTION

It has long been a feature of cosmetic compositions that they comprise a fragrance. The addition of a fragrance can mask unpleasant odours or can improve consumer acceptance of a composition through delivering a pleasant smell. Indeed, the sole purpose of some compositions is the application of a pleasant odour to the skin, hair or other suitable substrate. However, for the most part, the fragrant effect of these compositions is transitory and the fragrance quickly becomes imperceptible.

Attempts have been made to improve the longevity of the fragrance. For instance, the fragrance may be formulated in such a way as to include a higher proportion of fragrance materials with a low volatility. This means the fragrance persists for longer. However, using less volatile materials restricts the fragrance characters that can be achieved. It has also been suggested that it may be possible to utilise cyclic oligosaccharides and in particular cyclodextrins. For example, JP-A-50/63126 discloses perfume and cyclodextrin complexes for use in bath preparations and JP-A-7/241333 discloses a long-lasting, room deodorising composition containing a fragrance and cyclodextrin.

One drawback of using cyclic oligosaccharides is that they are only sparingly soluble in commonly used solvents. Attempts have been made to increase the solubility of cyclic oligosaccharides by introducing various substituents. See, for example, JP-A-6/287127, JP-A-8/176587, JP-A-10/120, 541, JP-A-62/161720 and JP-A-63/192706 all of which disclose compositions comprising perfume and substituted cyclodextrins.

Surprisingly, it has been found that compositions comprising fragrance and cyclic oligosaccharides having one or more unsubstituted alkyl substituents, wherein the weight ratio of fragrance to cyclic oligosaccharide is at least about 1:1, provide an initial burst of fragrance and improved fragrance longevity.

While not wishing to be bound by theory, it is believed that the fragrance material complexes with cyclic oligosaccharide of the present invention. It is believed that the stability profile of the complexes formed between the fragrance and the cyclic oligosaccharides of the present invention is such that a perceptible amount of fragrance is released over a sufficiently long time to satisfy the consumers desire for long lasting fragrance. In addition, it is believed that the weight ratio of fragrance to cyclic oligosaccharides in the present invention ensures that there is a 'burst' of fragrance on application of the composition to a suitable substrate.

SUMMARY OF THE INVENTION

According to the present invention there is provided fragrance compositions comprising:

(a) fragrance; and
(b) cyclic oligosaccharides having one or more unsubstituted alkyl substituents;
wherein the weight ratio of (a) to (b) is at least about 1:1.

The compositions of the present invention provide a long-lasting fragrance while at the same time having a 'burst' of fragrance on application.

All percentages herein are by weight of the composition unless otherwise indicated. All ratios are weight ratios unless otherwise indicated. Unless otherwise indicated, all percentages, ratios, and levels of ingredients referred to herein are based on the actual amount of the ingredient, and do not include solvents, fillers, or other materials which may be combined with the ingredient in commercially available products.

All documents referred to herein, including all patents, all patent applications and all articles, are hereby incorporated herein by reference in their entirety unless otherwise indicated.

DETAILED DESCRIPTION OF THE INVENTION

The present invention relates to compositions comprising fragrance and alkyl substituted cyclic oligosaccharides wherein the weight ratio of fragrance to cyclic oligosaccharide is at least about 1:1. Preferably the weight ratio of fragrance to cyclic oligosaccharide in the compositions of the present invention is at least about 1.2:1, more preferably at least about 1.5:1, even more preferably at least about 2:1.

Fragrance

An essential feature of the present compositions is that they comprise fragrance material. As used herein the term "fragrance" is used to indicate any odouriferous material. Any fragrance material suitable for use in cosmetic compositions may be used herein but the fragrance will most often be liquid at ambient temperatures. Generally, the fragrance material will be present at a level of from about 0.01% to about 40%, by weight, of total composition. Preferably the fragrance material is present at a level of from about 0.1% to about 25%, more preferably from about 1% to about 20%, even more preferably from about 5% to about 15%, by weight, of total composition.

A wide variety of chemicals are known for fragrance uses, including materials such as aldehydes, ketones and esters. More commonly, naturally occurring plant and animal oils and exudates comprising complex mixtures of various chemical components are known for use as fragrances. The fragrance materials useful herein include pro-fragrances such as acetal pro-fragrances, ketal pro-fragrances, ester pro-fragrances, hyrdolyzable inorganic-organic pro-fragrances and mixtures thereof. The fragrance material may be released from the pro-fragrances in a number of ways. For example, the fragrance may be released as a result of simple hydrolysis, or by a shift in an equilibrium reaction, or by a pH-change, or by enzymatic release. The fragrances herein can be relatively simple in their compositions, comprising a single chemical, or can comprise highly sophisticated complex mixtures of natural and synthetic chemical components, all chosen to provide any desired odour.

Preferably the fragrance materials of the present invention will have boiling points (BP) of about 500° C. or lower, more preferably about 400° C. or lower, even more preferably about 350° C. or lower. The BP of many fragrance materials are given in *Perfume and Flavor Chemicals* (Aroma Chemicals), Steffen Arctander (1969). The ClogP value of the fragrance materials useful herein is preferably greater than about 0.1, more preferably greater than about 0.5, even more preferably greater than about 1.0, even more preferably still greater than about 1.2. As used herein the term "ClogP" means the logarithm to the base 10 of the octanol/water partition coefficient. This can be readily calculated from a program called "CLOGP" which is available from Daylight Chemical Information Systems Inc., Irvine Calif., USA. Octanol/water partition coefficients are described in more detail in U.S. Pat. No. 5,578,563.

Suitable fragrance materials can be found in U.S. Pat. No. 4,145,184, U.S. Pat. No. 4,209,417, U.S. Pat. No. 4,515,705, and U.S. Pat. No. 4,152,272. Examples of fragrances useful herein include, but are not limited to, animal fragrances such as musk oil, civet, castoreum, ambergris, plant fragrances such as nutmeg extract, cardomon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomille oil, clove oil, sage oil, neroli oil, labdanum oil, eucalyptus oil, verbena oil, mimosa extract, narcissus extract, carrot seed extract, jasmine extract, olibanum extract, rose extract and mixtures thereof.

Other examples of suitable fragrance materials include, but are not limited to, chemical substances such as acetophenone, adoxal, aldehyde C-12, aldehyde C-14, aldehyde C-18, allyl caprylate, ambroxan, amyl acetate, dimethylindane derivatives, α-amylcinnamic aldehyde, anethole, anisaldehyde, benzaldehyde, benzyl acetate, benzyl alcohol and ester derivatives, benzyl propionate, benzyl salicylate, borneol, butyl acetate, camphor, carbitol, cinnamaldehyde, cinnamyl acetate, cinnamyl alcohol, cis-3-hexanol and ester derivatives, cis-3-hexenyl methyl carbonate, citral, citronnellol and ester derivatives, cumin aldehyde, cyclamen aldehyde, cyclo galbanate, damascones, decalactone, decanol, estragole, dihydromyrcenol, dimethyl benzyl carbinol, 6,8-dimethyl-2-nonanol, dimethyl benzyl carbinyl butyrate, ethyl acetate, ethyl isobutyrate, ethyl butyrate, ethyl propionate, ethyl caprylate, ethyl cinnamate, ethyl hexanoate, ethyl valerate, ethyl vanillin, eugenol, exaltolide, fenchone, fruity esters such as ethyl 2-methyl butyrate, galaxolide, geraniol and ester derivatives, helional, 2-heptonone, hexenol, α-hexylcinnamic aldehyde, hydroxycitrolnellal, indole, isoamyl acetate, isoeugenol acetate, ionones, isoeugenol, isoamyl iso-valerate, iso E super, limonene, linalool, lilial, linalyl acetate, lyral, majantol, mayol, melonal, menthol, p-methylacetophenone, methyl anthranilate, methyl cedrylone, methyl dihydrojasmonate, methyl eugenol, methyl ionone, methyl-α-naphthyl ketone, methylphenylcarbinyl acetate, mugetanol, γ-nonalactone, octanal, phenyl ethyl acetate, phenyl-acetaldehyde dimethyl acetate, phenoxyethyl isobutyrate, phenyl ethyl alcohol, pinenes, sandalore, santalol, stemone, thymol, terpenes, triplal, triethyl citrate, 3,3,5-trimethylcyclohexanol, γ-undecalactone, undecenal, vanillin, veloutone, verdox and mixtures thereof.

Cyclic Oligosaccharides

A second essential element of the compositions of the present invention is that they comprise cyclic oligosaccharides having one or more unsubstituted alkyl substituents. As used herein, the term "cyclic oligosaccharide" means a cyclic structure comprising six or more saccharide units. Preferred for use herein are cyclic oligosaccharides having six, seven or eight saccharide units and mixtures thereof, more preferably seven saccharide units. It is common in the art to abbreviate six, seven and eight membered cyclic oligosaccharides to α, β and γ respectively.

The cyclic oligosaccharides herein are preferably present at a level of from about 0.001% to about 40%, more preferably from about 0.1% to about 25%, even more preferably from about 1% to about 20%, especially from about 2% to about 15%, by weight, of total composition.

The cyclic oligosaccharides of the present invention may comprise any suitable saccharide or mixtures of saccharides. Examples of suitable saccharides include, but are not limited to, glucose, fructose, mannose, galactose, maltose and mixtures thereof. However, preferred for use herein are cyclic oligosaccharides of glucose. Therefore, the preferred cyclic oligosaccharides for use herein are β-cyclodextrins.

The cyclic oligosaccharides for use herein must have one or more unsubstituted alkyl substituents. The alkyl substituent may be saturated or unsaturated, straight or branched chain but is preferably saturated and straight chain. Preferably, the alkyl substituent is selected from $C_1$–$C_8$ alkyl groups and mixtures thereof, more preferably the alkyl substituent is selected from $C_1$–$C_6$ alkyl groups and mixtures thereof, even more preferably the alkyl substituent is selected from $C_1$–$C_4$ alkyl groups and mixtures thereof. Preferred alkyl substituents are ethyl and methyl, especially methyl. Therefore, the most preferred cyclic oligosaccharides for use herein are methyl-β-cyclodextrins.

The cyclic oligosaccharides of the present invention are preferably substituted only by the unsubstituted alkyl substituents mentioned hereinabove. However, they may be substituted by other substituents. Examples of other suitable substituents include, but are not limited to, hydroxyalkyl groups, aryl groups, maltosyl groups, allyl groups, benzyl groups, alkanoyl groups and mixtures thereof.

Methods of modifying cyclic oligosaccharides are well known in the art. For example, see "*Methods of Selective Modifications of Cyclodextrins*" Chemical Reviews (1998) Vol. 98, No.5, pp 1977–1996, Khan et al and U.S. Pat. No. 5,710,268. In addition, methyl-β-cyclodextrins are available from Wacker-Chemie GmbH Hanns-Seidel-Platz 4, Munchen, Del. under the tradename Beta W7 M 1.8.

The cyclic oligosaccharides of the present invention preferably have an average degree of substitution of from about 0.5 to about 3.0, more preferably from about 1.0 to about 2.8, even more preferably from about 1.2 to about 2.3, especially from about 1.6 to about 1.9. As used herein the term "degree of substitution" means the average number of substituents per saccharide unit. The average number of substituents can be determined using Nuclear Magnetic Resonance techniques common in the art.

The cyclic oligosaccharides of the present invention are preferably soluble in both water and ethanol. As used herein "soluble" means at least about 0.1 g of solute dissolves in 100 ml of solvent, at 25° C. and 1 atm of pressure. Preferably the cyclic oligosaccharides for use herein have a solubility of at least about 1 g/100 ml, more preferably at least about 10 g/100 ml, even more preferably at least about 100 g/100 ml, at 25° C. and 1 atm of pressure.

Optional Ingredients

The compositions herein can contain a variety of other optional components suitable for rendering such compositions more cosmetically or aesthetically acceptable or to provide them with additional usage benefits. Such conventional optional ingredients are well-known to those skilled in the art. These include any cosmetically acceptable ingredients such as those found in the CTFA *International Cosmetic Ingredient Dictionary and Handbook,* 7th edition, edited by Wenninger and McEwen, (*The Cosmetic, Toiletry, and Fragrance Association*, Inc., Washington, D.C., 1997). As used herein "cosmetically acceptable" means a material (e.g., compound or composition) which is suitable for use in contact with skin, hair or other suitable substrate as defined hereinbelow.

Cosmetically Acceptable Carrier

The compositions of the present invention will preferably comprise a cosmetically acceptable carrier. The phrase "cosmetically acceptable carrier", as used herein, means one or more compatible solid or liquid fillers, diluents, extenders and the like, which are cosmetically acceptable as defined hereinabove. The term "compatible", as used herein, means that the components of the compositions of this invention are capable of being combined with the primary actives of the present invention, and with each other, in a manner such that there is no interaction which would substantially reduce the efficacy of the composition under ordinary use situations. The type of carrier utilized in the present invention depends on the type of product desired. The compositions useful in the present invention may be a wide variety of product types. These include, but are not limited to, lotions, creams, gels, sticks, sprays, ointments, pastes, mousses and cosmetics (e.g., solid, semi-solid, or liquid make-up, including foundations). These product types may comprise several types of carriers including, but not limited to, solutions, aerosols, emulsions (including oil-in-water or water-in-oil), gels, solids, and liposomes.

Volatile Solvent

The compositions of the present invention may also comprise one or more volatile solvent. If present, the volatile solvent or mixture of solvents will generally be at a level of about 5% or greater, preferably about 10% or greater, more preferably about 20% or greater, even more preferably about 50% or greater, by weight of total composition. The solvents useful herein are preferably organic volatile solvents.

As used herein, "volatile" refers to substances with a significant amount of vapour pressure under ambient conditions, as is understood by those in the art. The volatile solvents for use herein will preferably have a vapour pressure of about 2 kPa or more, more preferably about 6 kPa or more, at 25° C. The volatile solvents for use herein will preferably have a boiling point under one atmosphere (atm) of less than about 150° C., more preferably less than about 100° C., even more preferably less than about 90° C., even more preferably still less than about 80° C.

Preferably the volatile solvents for use herein will be relatively odourless and safe for use on human skin. Suitable volatile solvents include, but are not limited to, $C_1$–$C_4$ alcohols, volatile silicones and mixtures thereof. Preferred volatile solvents are $C_1$–$C_4$ alcohols and mixtures thereof. More preferred for use herein is ethanol.

Nonvolatile Solvents

While the compositions of the present invention preferably comprise a volatile solvent they may also comprise "nonvolatile" solvents. Suitable non-volatile solvents include, but are not limited to, benzyl benzoate, diethyl phthalate, isopropyl myristate, and mixtures thereof.

Molecular Wedges

Particularly preferred for use herein for providing increased longevity and strength of odour of fragrance is a low molecular weight polyol molecular wedge having from about 2 to about 12 carbon atoms, preferably from about 2 to about 6 carbon atoms and at least one —OH functional group, preferably at least 2-OH functional groups. These polyols can further contain ether groups within the carbon chain. Suitable examples include ethylene glycol, propylene glycol, dipropylene glycol, 1,4-butanediol, 1,6-hexanediol and mixtures thereof. When present these polyols are present at a level of from about 0.01% to about 20%, preferably from about 0.1% to about 10%, and especially from about 0.5% to about 5% by weight of composition. It is preferred that the molar ratio of molecular wedge material to oligosaccharide is from 10:1 to 1:10, preferably 1:1 or greater, especially 1:1.

While not wishing to be limited by theory, the above mentioned molecular wedge molecules form tertiary inclusion complexes with the complexed perfume material and the cyclic oligosaccharide. These small dipolar molcules can fit into the cavity of the cyclic oligosaccharide and anchor via their OH groups onto the outside rim of the cyclic oligosaccharide through hydrogen bonding. This enables the inclusion of all or parts of the fragrance material into the cavity of the cyclic oligosaccharide such that the stability of the formed tertiary complex is increased versus the complex formed by the fragrance material and cyclic oligosaccharide alone.

Water

The compositions of the present invention may also comprise water. If present, the water will preferably comprise from about 0.1% to about 40%, more preferably from about 1% to about 30%, even more preferably about 5% to about 20%, by weight, of total composition.

There are a number of other examples of additional ingredients that are suitable for inclusion into the present compositions. These include, but are not limited to, alcohol denaturants such as denatonium benzoate; UV stabilisers such as benzophenone-2; antioxidants such as tocopheryl acetate; preservatives such as phenoxyethanol, benzyl alcohol, methyl paraben, propyl paraben; dyes; pH adjusting agents such as lactic acid, citric acid, sodium citrate, succinic acid, phosphoric acid, sodium hydroxide, sodium carbonate; deodorants and antimicrobials such as farnesol and zinc phenolsulphonate; humectants such as glycerine; oils; skin conditioning agents such as allantoin; cooling agents such as trimethyl isopropyl butanamide and menthol; hair conditioning ingredients such as panthenol, panthetine, pantotheine, panthenyl ethyl ether, and combinations thereof; silicones; solvents such as hexylene glycol; hair-hold polymers such as those described in WO-A-94/08557; salts in general, such as potassium acetate and sodium chloride and mixtures thereof. If present, these additional ingredients will preferably be present at a level of less than 10%, by weight, of total composition. More preferably these additional ingredients will be present at a level of less than 5%, by weight, of total composition.

Methods of Use

The compositions of the present invention can be used to provide a long-lasting fragrance to a suitable substrate. As used herein the term "suitable substrate" means any surface to which the present composition may be applied without an unduly adverse effect. Suitable substrates include, but are not limited to, skin, hair and fabrics. Preferably the present compositions are applied to skin or hair, especially skin.

The cosmetic compositions of the present invention may be used in a conventional manner for fragrancing a suitable substrate. An effective amount of the composition, typically from about 1 μL to about 1000 μl, preferably from about 10 μl to about 250 μl, more preferably from about 25 μl to about 100 μl, is applied to the substrate. The composition may be applied by hand but is preferably applied utilising a vaporiser. Preferably, the composition is then left to dry.

Therefore, the preferred method of treating the substrate comprises:

(a) applying an effective amount of the composition to a suitable substrate; and preferably (b) allowing the composition to dry.

Product Forms

The compositions of the present invention may take any form suitable for cosmetic use. These include, but are not limited to, vapour sprays, aerosols, emulsions, solid sticks, lotions and liquids. Preferably the compositions of the present invention take the form of a vapour spray.

EXAMPLES

The following examples further illustrate the preferred embodiments within the scope of the present invention. The examples are given solely for the purposes of illustration and are not to be construed as limitations of the present invention as many variations of the invention are possible without departing from its spirit or scope. Unless otherwise indicated, all ingredients are expressed on a weight percentage of the active ingredient.

|  | I (% wt) Vapour Spray | II (% wt) Vapour Spray | III (% wt) Vapour Spray |
| --- | --- | --- | --- |
| Fragrance | 15 | 12.5 | 10 |
| Cyclic oligosaccharide[1] | 5 | 7.5 | 10 |
| Ethanol | 70 | 70 | 70 |
| Deionised Water | 10 | 10 | 10 |

[1]Beta W7 M1.8 available from Wacker-Chemie GmbH, Hanns-Seidel-Platz 4, Munchen, DE The cyclic oligosaccharide was dissolved in the ethanol at room temperature, with stirring. Then the fragrance and water were added with stirring.

|  | IV (% wt) Liquid Perfume | V (% wt) Liquid Perfume | VI (% wt) Liquid Perfume |
| --- | --- | --- | --- |
| Fragrance | 15 | 12.5 | 10 |
| Cyclic oligosaccharide[1] | 5 | 7.5 | 10 |
| Ethanol | 80 | 80 | 80 |

[1]Beta W7 M1.8 available from Wacker-Chemie GmbH, Hanns-Seidel-Platz 4, Munchen, DE The cyclic oligosaccharide was dissolved in the ethanol at room temperature, with stirring. Then the fragrance was added with stirring.

|  | VII (% wt) Deodorant | VIII (% wt) Deodorant | IX (% wt) Deodorant |
| --- | --- | --- | --- |
| Fragrance | 3 | 2.5 | 3 |
| Cyclic oligosaccharide[1] | 1.5 | 2 | 1.5 |
| Zinc phenolsulphonate | 2 | 1 | 2 |
| Dipropylene Glycol | 31 | 17.5 | 27 |
| Isopropyl myristate | 1.5 | 7 | 1.5 |
| Ethanol | 61 | 70 | 65 |

[1]Beta W7 M1.8 available from Wacker-Chemie GmbH, Hanns-Seidel-Platz 4, Munchen, DE The zinc phenolsulphonate is stirred into the ethanol until fully dissolved. Then the dipropylene glycol is added with stirring. Next the isopropyl myristate, then the cyclic oligosaccharide and then the fragrance are all added with stirring. All steps are performed at room temperature. For an aerosol deodorant a propellant such as propane butane (CAP 40®) can be added to Examples VII–IX according to standard industry practice.

Examples X–XI

|  | X (% wt) Vapour Spray | XI (% wt) Vapour Spray |
| --- | --- | --- |
| Fragrance | 15 | 15 |
| Cyclic oligosaccharide[1] | 5 | 5 |
| Ethanol | 70 | 70 |
| Deionised Water | to 100 | to 100 |
| dipropylene glycol | 5 | 2.5 |
| ethylene glycol | 0 | 2.5 |

[1]Beta W7 M1.8 available from Wacker-Chemie GmbH, Hanns-Seidel-Platz 4, Munchen, DE The cyclic oligosaccharide was dissolved in the ethanol at room temperature, with stirring. Then the fragrance, dipropylene glycol/ethylene glycol and water were added with stirring.

All of the above examples were found to give an initial 'burst' of fragrance and have long-lasting fragrance.

What is claimed is:

1. A cosmetic composition comprising:

(a) fragrance;

(b) cyclic oligosaccharides having one or more unsubstituted alkyl substituents; and (c) about 20% or greater of a volatile solvent; and wherein the weight ratio of (a) to (b) is greater than about 1:1.

2. A composition according to claim 1 wherein the weight ratio of fragrance to cyclic oligosaccharide is at least about 1.2:1.

3. A composition according to claim 1 wherein said cyclic oligosaccharide has an average degree of substitution of from about 0.5 to 3.0.

4. A composition according to claim 1 wherein said alkyl substituent is selected from $C_1$–$C_8$ alkyl groups and mixtures thereof.

5. A composition according to claim 1 wherein said alkyl substituent is a methyl group.

6. A composition according to claim 1 wherein said solvent is selected from $C_1$–$C_4$ alcohols and mixtures thereof.

7. A composition according to claim 1 wherein said cyclic oligosaccharide has six, seven or eight saccharide units and mixtures thereof.

8. A composition according to claim 1 wherein said cyclic oligosaccharide is a cyclodextrin.

9. A composition according to claim 1 comprising a polyol having from about 2 to about 12 carbon atoms and at least one —OH group.

10. A composition according to claim 9 wherein the polyol is selected from ethylene glycol, propylene glycol, dipropylene glycol, 1,4 butanediol and 1,6 hexanediol, and mixtures thereof.

11. A cosmetic method of fragrancing mammalian skin comprising:

(a) applying a composition according to claim 1 to the skin, hair or other suitable substrate; and preferably (b) allowing said composition to dry.

* * * * *